(12) United States Patent
Magera et al.

(10) Patent No.: US 9,719,884 B2
(45) Date of Patent: Aug. 1, 2017

(54) INTAKE GAS SENSOR FOR INTERNAL COMBUSTION ENGINE

(71) Applicant: Robert Bosch GmbH, Stuttgart (DE)

(72) Inventors: Craig Magera, Simpsonville, SC (US);
Claus Schnabel, Fenton, MI (US);
David Boyd, Greenville, SC (US)

(73) Assignee: Robert Bosch GmbH, Stuttgart (DE)

( * ) Notice: Subject to any disclaimer, the term of this patent is extended or adjusted under 35 U.S.C. 154(b) by 734 days.

(21) Appl. No.: 13/835,897

(22) Filed: Mar. 15, 2013

(65) Prior Publication Data
US 2014/0174165 A1 Jun. 26, 2014

Related U.S. Application Data

(60) Provisional application No. 61/739,959, filed on Dec. 20, 2012, provisional application No. 61/739,949, filed on Dec. 20, 2012.

(51) Int. Cl.
*G01M 15/00* (2006.01)
*G01M 15/04* (2006.01)
*G01N 27/407* (2006.01)

(52) U.S. Cl.
CPC ........ *G01M 15/04* (2013.01); *G01N 27/4078* (2013.01)

(58) Field of Classification Search
CPC ............ F02D 2200/0406; F02D 41/18; F02D 2200/0402; F02D 2200/0414; Y02T 10/40; G01M 15/04
USPC ...................................................... 73/114.31
See application file for complete search history.

(56) References Cited

U.S. PATENT DOCUMENTS

| 3,960,692 A | 6/1976 | Weyl et al. |
| 4,123,131 A | 10/1978 | Pearce, Jr. et al. |
| 4,283,261 A | 8/1981 | Maurer et al. |
| 4,560,463 A * | 12/1985 | Frey .................. G01N 27/4067 204/424 |
| 4,802,369 A | 2/1989 | Morii |
| 4,860,603 A | 8/1989 | Russoniello |

(Continued)

FOREIGN PATENT DOCUMENTS

| WO | 2004048955 | 6/2004 | |
| WO | WO 2004048955 A2 * | 6/2004 | ............. G01N 27/00 |

OTHER PUBLICATIONS

International Search Report for International Appl. No. PCT/US2013/075338 dated Apr. 2, 2014, 5 pages.

(Continued)

*Primary Examiner* — Laura Martin
*Assistant Examiner* — Mohammed E Keramet-Amircola
(74) *Attorney, Agent, or Firm* — Michael Best & Friedrich LLP

(57) ABSTRACT

A gas sensor includes a gas sensing element positioned at least partially within a body and being exposed at a first end to measure a gas in contact with the first end. A sleeve is fixed to the body and extends from the body in a direction opposite the first end of the gas sensing element. The sleeve includes it remote end portion having an engagement feature. A connector housing is overmolded onto the end portion of the sleeve to lock onto the sleeve via the engagement feature. The connector housing includes a plug connector portion partially enclosing a plurality of electrical terminals electrically connected to the gas sensing element.

20 Claims, 12 Drawing Sheets

(56) References Cited

U.S. PATENT DOCUMENTS

| | | | |
|---|---|---|---|
| 5,582,797 A | | 12/1996 | Kewley et al. |
| 5,722,634 A | | 3/1998 | Hrytzak et al. |
| 5,817,920 A | | 10/1998 | Kuisell et al. |
| 5,821,401 A | | 10/1998 | Awarzamani et al. |
| 5,918,275 A | | 6/1999 | Kato et al. |
| 6,068,746 A | * | 5/2000 | Kojima ............... G01N 27/407 204/421 |
| 6,116,224 A | | 9/2000 | Cook et al. |
| 6,223,733 B1 | | 5/2001 | Busato et al. |
| 6,359,439 B1 | | 3/2002 | Crecelius et al. |
| 6,571,782 B2 | | 6/2003 | Brosseau et al. |
| 6,629,521 B1 | | 10/2003 | Kato |
| 6,658,918 B2 | | 12/2003 | Hibino et al. |
| 6,978,754 B2 | | 12/2005 | Cicone |
| 7,258,770 B2 | | 8/2007 | Weyl et al. |
| 8,001,827 B2 | * | 8/2011 | Weyl ................. G01N 27/4077 73/23.31 |
| 8,147,667 B2 | | 4/2012 | Robison |
| 8,318,525 B2 | * | 11/2012 | Davies .................. G01N 27/16 422/83 |
| 2001/0045206 A1 | | 11/2001 | Smith et al. |
| 2004/0231441 A1 | * | 11/2004 | Wu .............................. 73/866.5 |
| 2009/0065358 A1 | * | 3/2009 | Matsumoto ................... 204/424 |
| 2010/0170794 A1 | * | 7/2010 | Gibson .............. G01N 27/4062 204/406 |
| 2012/0018305 A1 | | 1/2012 | Yoshikawa et al. |
| 2012/0055234 A1 | | 3/2012 | Yonezu et al. |
| 2013/0074578 A1 | * | 3/2013 | Yonezu et al. ............... 73/23.31 |

OTHER PUBLICATIONS

Written Opinion for International Appl. No. PCT/US2013/075338 dated Apr. 2, 2014, 8 pages.

Anonymous: "PPS 40% Glass Filled (Polyphenylene Sulfide)" by Sterling Plastics, Inc., retrieved from website url: http://sterlingplasticsinc.com/materials/pps-40-glass-filled-quadrant-polyphenylene-sulfide/, Jan. 12, 2012, 2 pages.

Anonymous: "BASF Ultradur B 4300 G4 20% Glass Filled PBT" retrieved from website url:http://www.matweb.com/search/datasheet.aspx?matguid=9f380f0b64aa45298d2698419e8c403c&ckck=1, 3/2514, 3 pages.

Getelec, "Thermoplastic overmolding," <http://en.getelec.com/emc-solutions/thermoplastic-overmolding/>, web page accessed Feb. 16, 2017.

Manufacturing Terms, "Overmolding," <http://www.manufacturingterms.com/Overmolding.html>, web page accessed Feb. 16, 2017.

Design-Tek Tool & Plastics Inc., "What is Overmolding? The versatility of Overmolding," <http://designtekplastics.com/tips/what-is-overmolding/>, dated Oct. 26, 2013.

Creative Mechanisms, "Everything You Need to Know About Overmolding Prototypes," <https://www.creativemechanisms.com/blog/overmolding-prototype-design-development>, web page accessed Feb. 16, 2017.

GLS Corporation, "Overmolding Guide," <www.polyone.com/files/resources/Overmold_Design_Guide.pdf>, web page accessed Feb. 16, 2017.

* cited by examiner

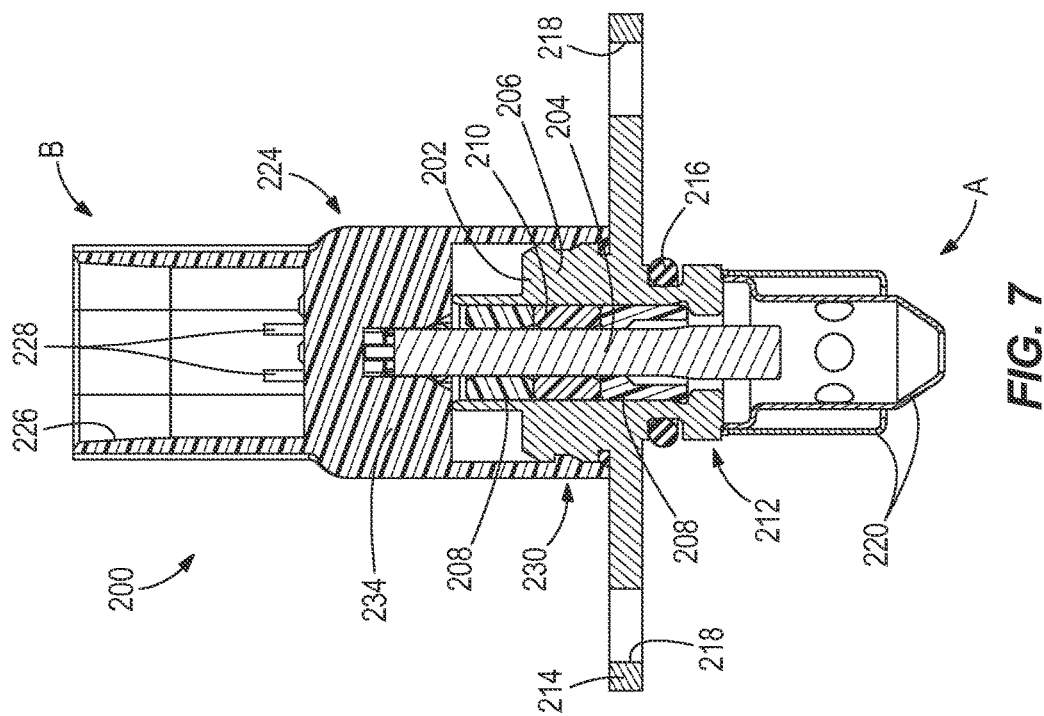
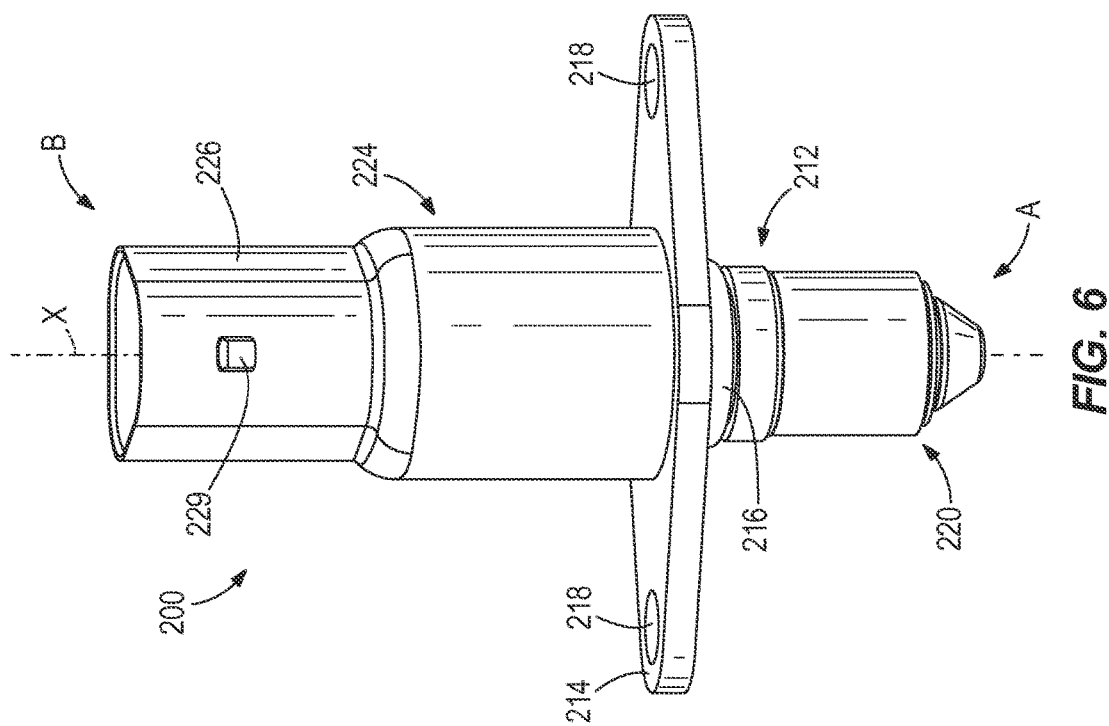

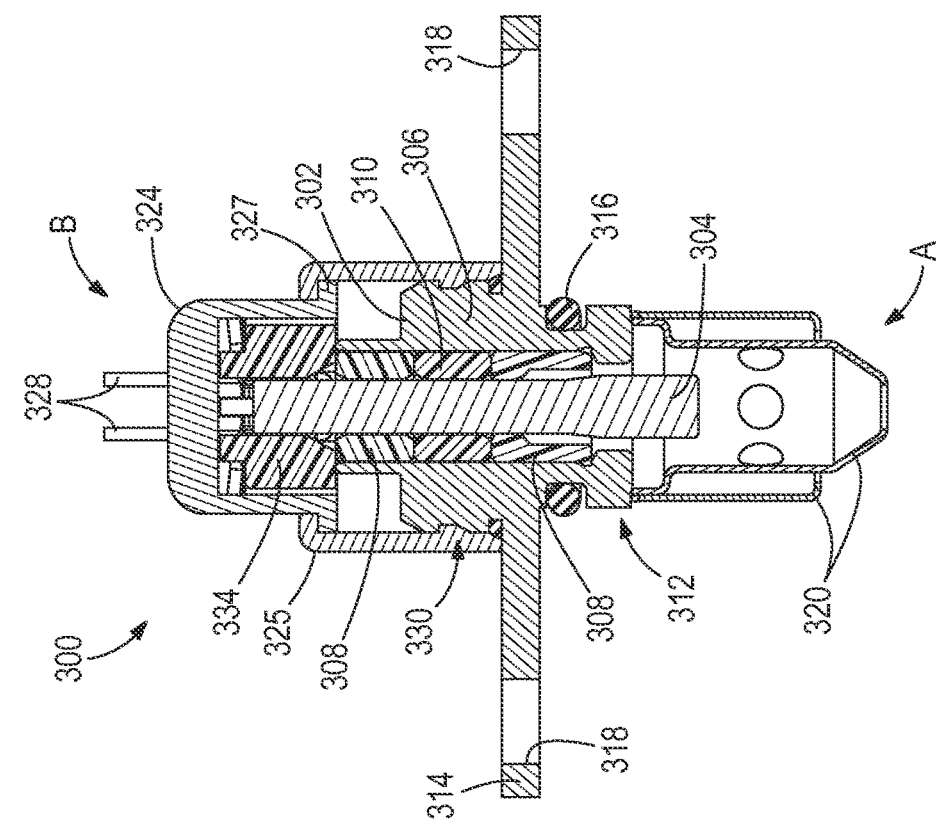
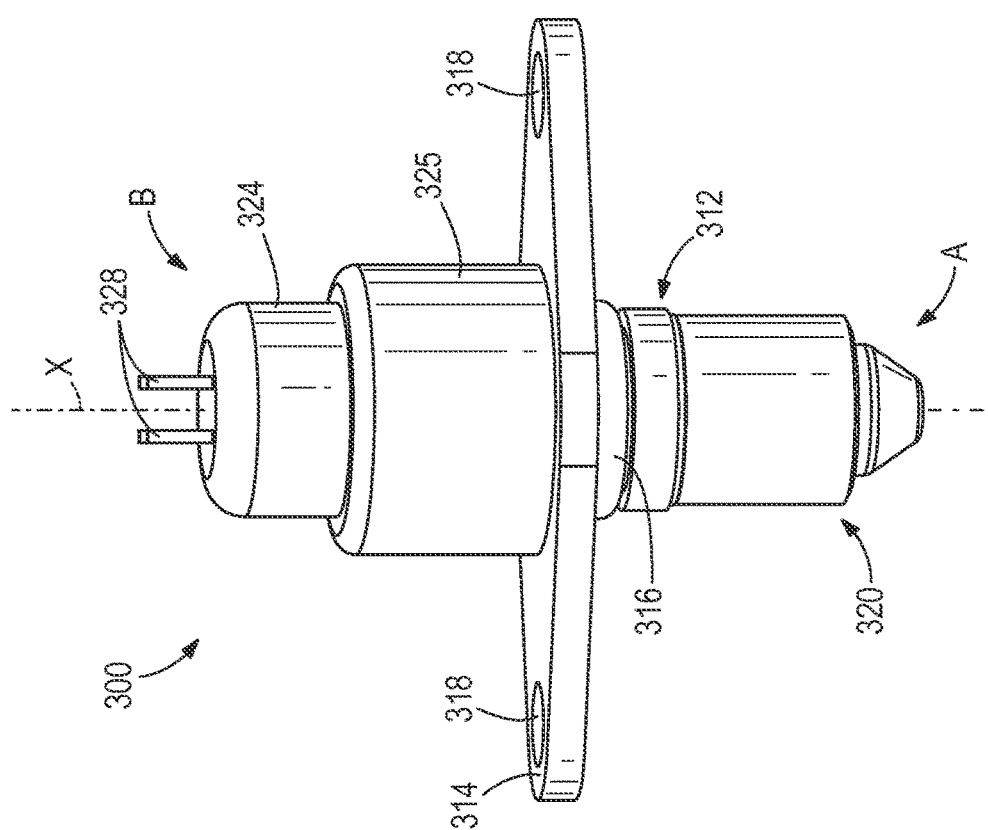

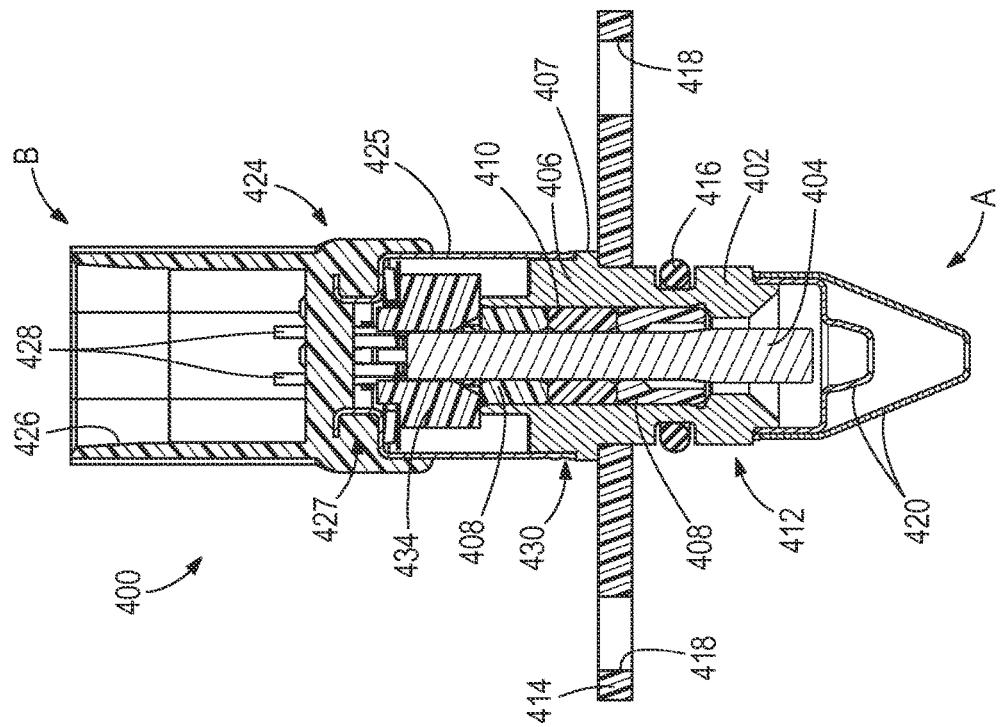
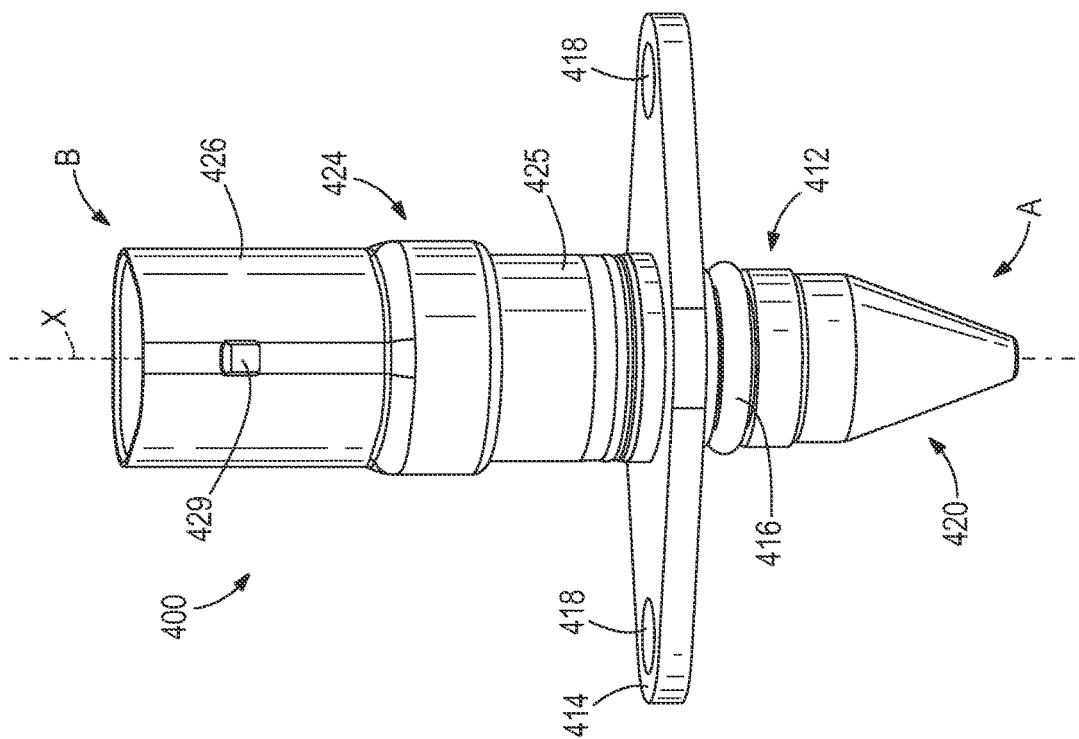

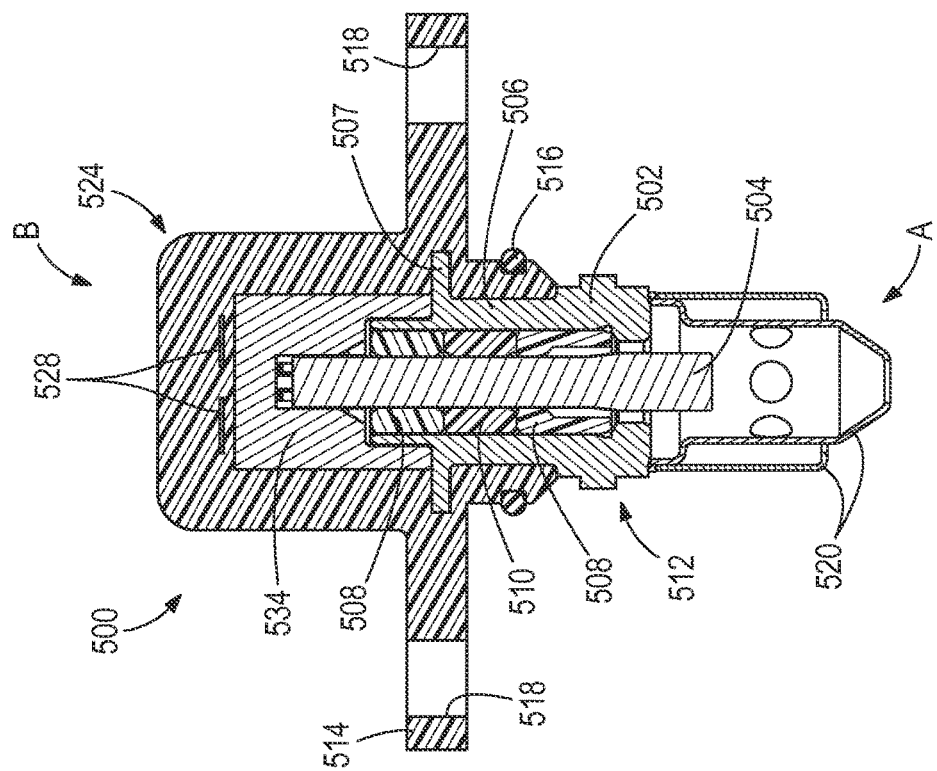
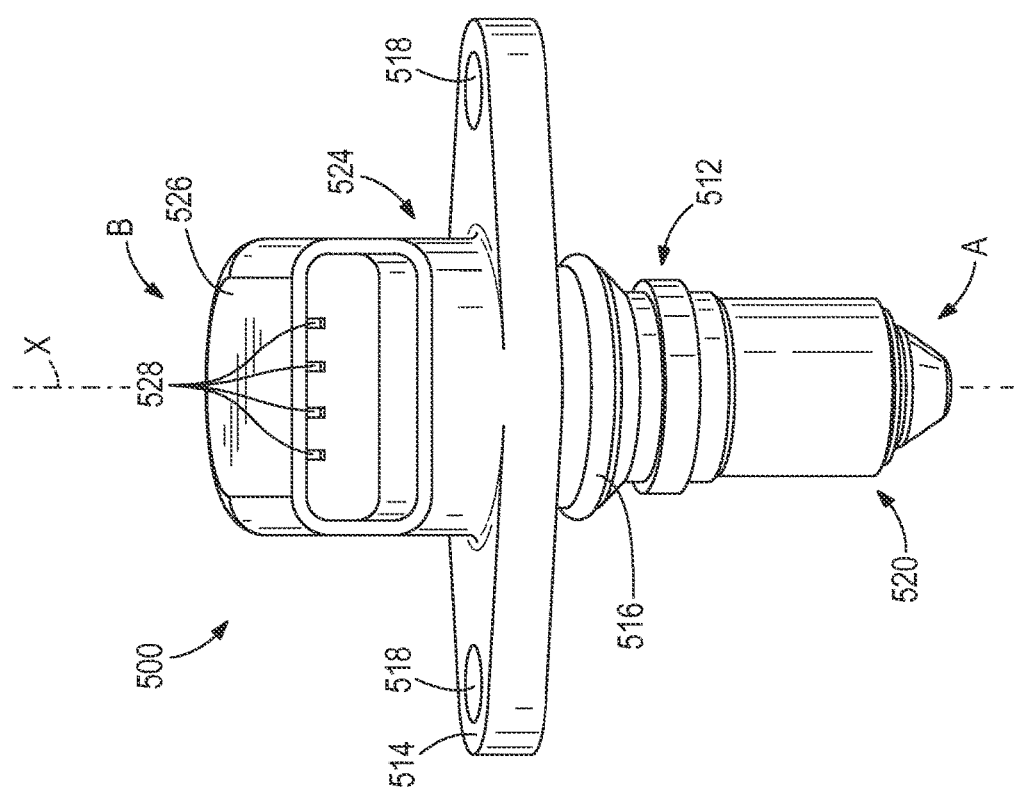

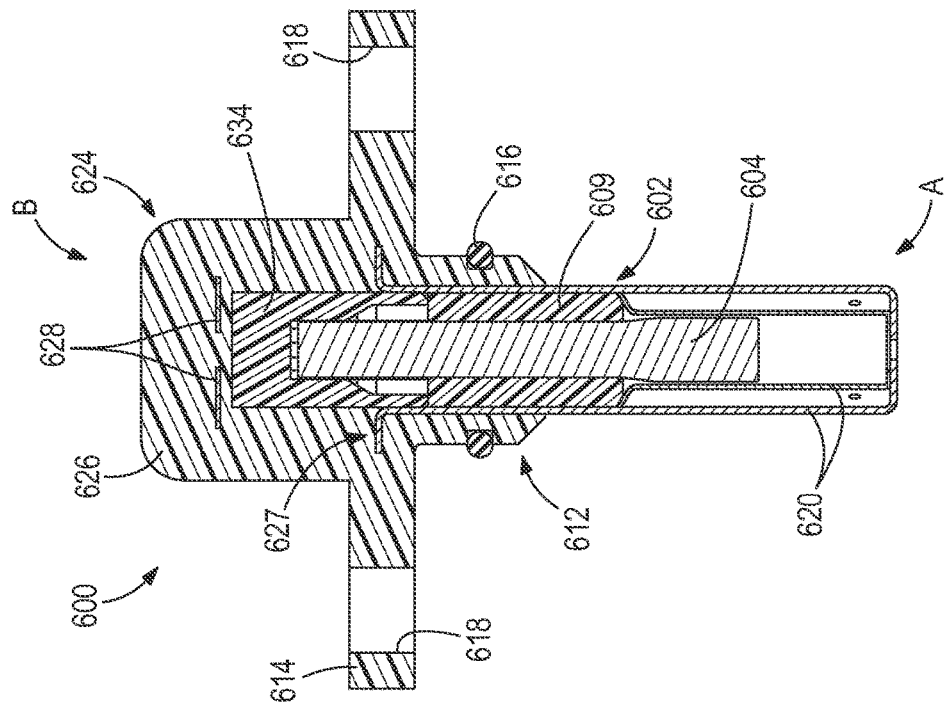
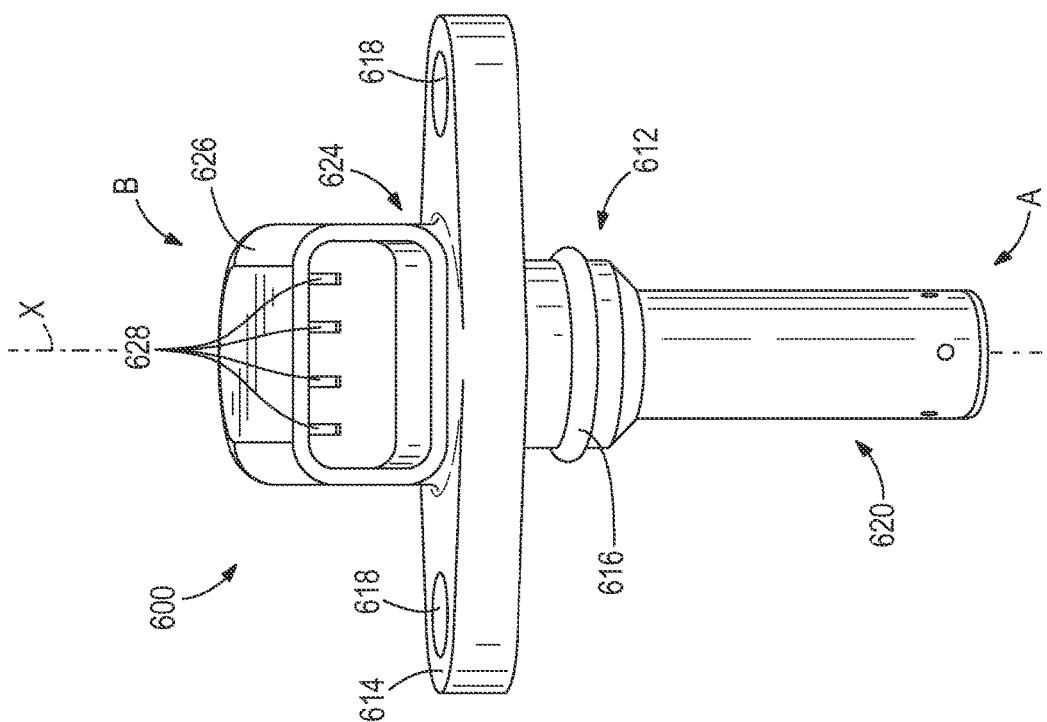

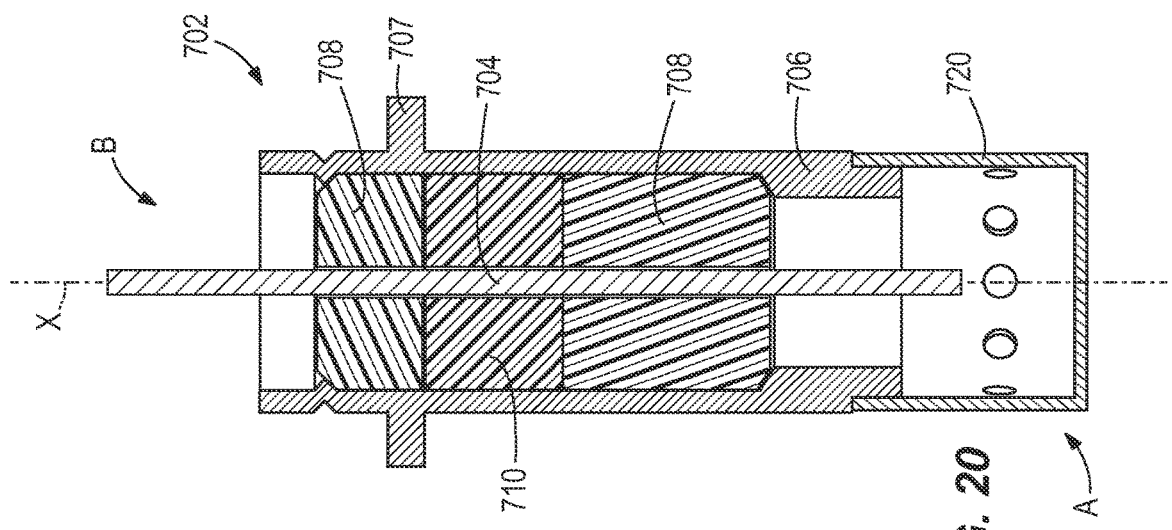
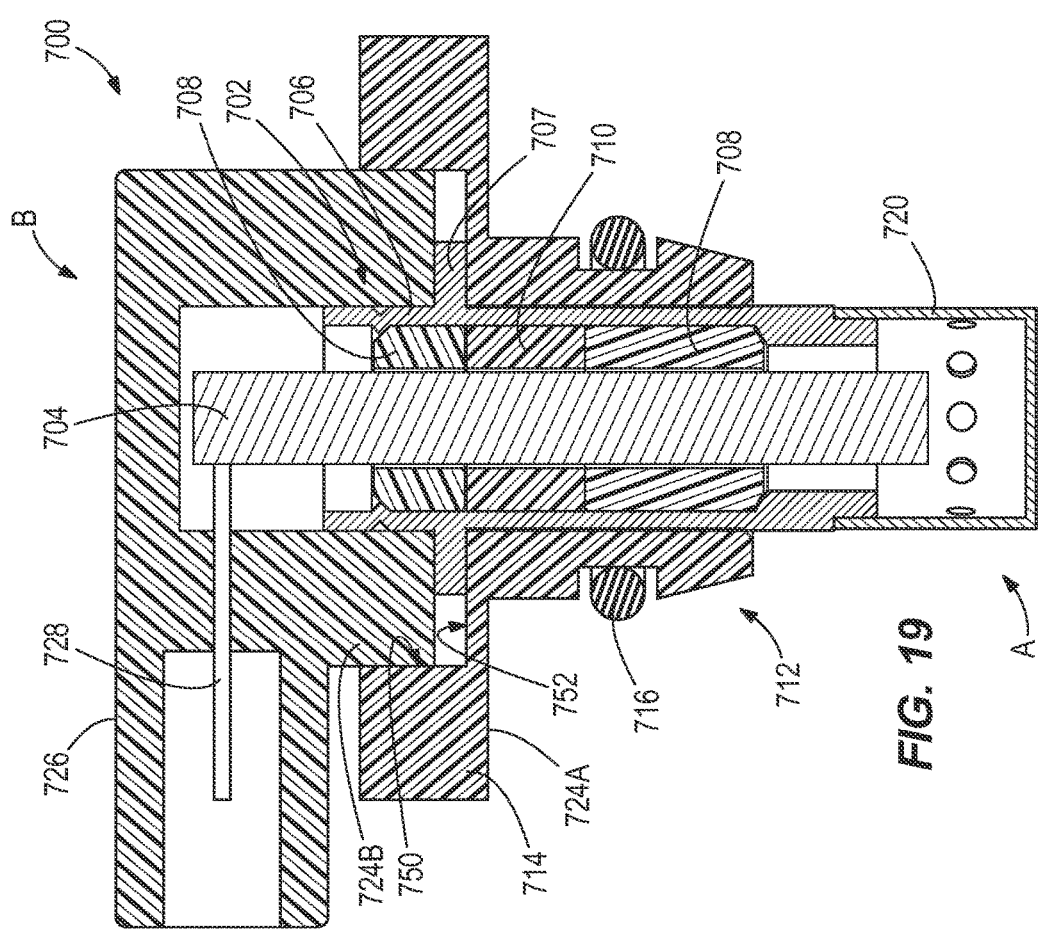

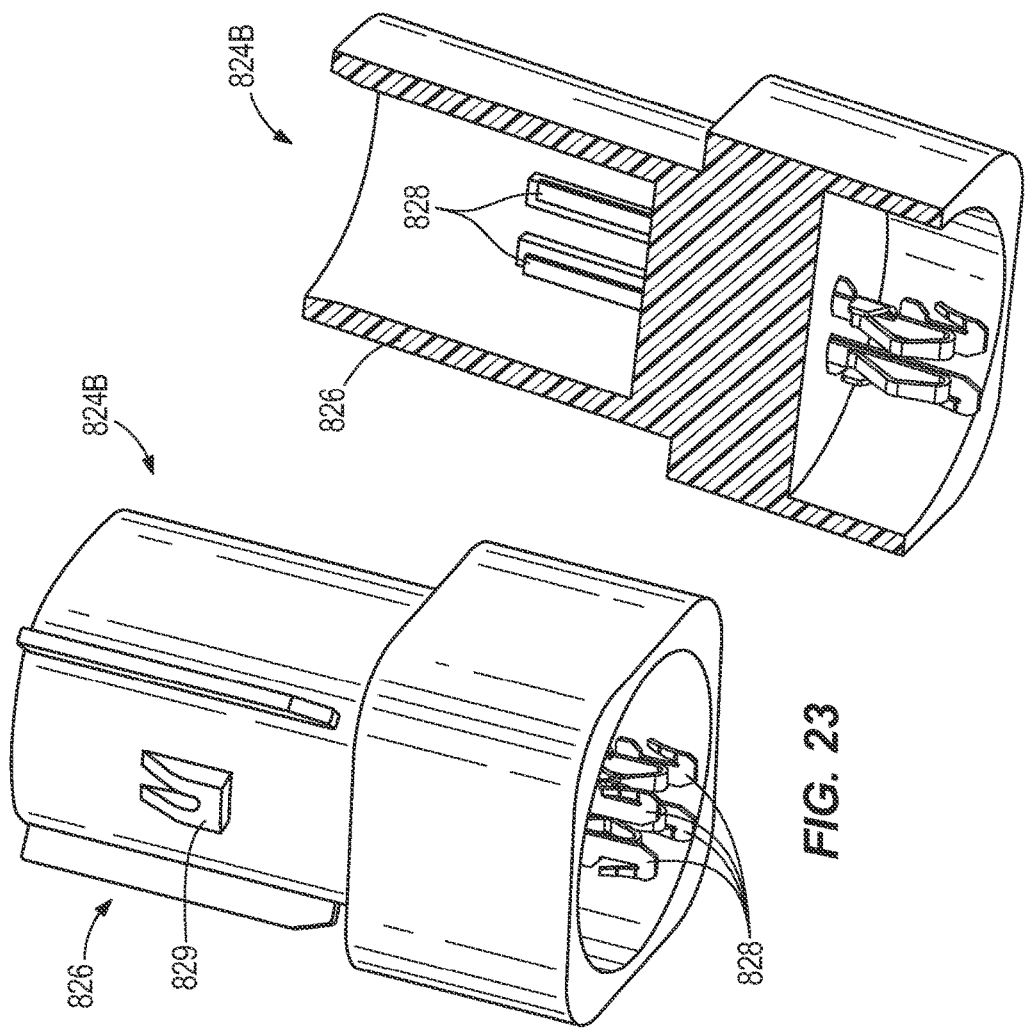
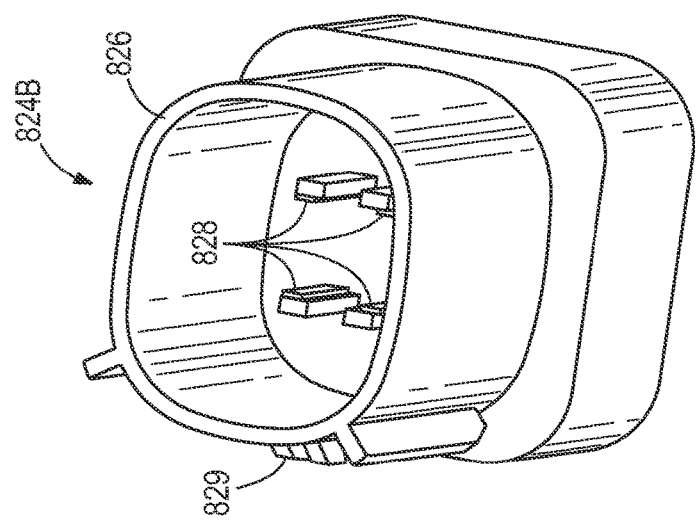

US 9,719,884 B2

INTAKE GAS SENSOR FOR INTERNAL COMBUSTION ENGINE

CROSS-REFERENCE TO RELATED APPLICATIONS

This application claims priority to U.S. Patent Application No. 61/739,949, filed Dec. 20, 2012 and U.S. Patent Application No. 61/739,959, filed Dec. 20, 2012 the entire contents of both of which are hereby incorporated by reference.

BACKGROUND

The present invention relates to various gas (e.g., oxygen) sensor designs for low temperature environments, having various plastic connector housing designs. Low temperature means low relative to the high temperature exhaust system where oxygen sensors are typically mounted. Currently oxygen sensors are designed for high temperature applications. The sensors are mounted in exhaust manifolds or exhaust systems. Oxygen sensors are designed for exposure to exhaust gas of 1030 C or more, mounting surface temperatures of 700 C and cable outlet temperatures of 280 C. This requires high temperature stainless steel alloys and high temperature rubber sealing materials. These materials are expensive due to their high thermal capabilities.

SUMMARY

In one aspect, the invention provides a gas sensor including a gas sensing element positioned at least partially within a body and being exposed at a first end to measure a gas in contact with the first end. A sleeve is fixed to the body and extends from the body in a direction opposite the first end of the gas sensing element. The sleeve includes a remote end portion having an engagement feature. A connector housing is overmolded onto the end portion of the sleeve to lock onto the sleeve via the engagement feature. The connector housing includes a plug connector portion partially enclosing a plurality of electrical terminals electrically connected to the gas sensing element.

In another aspect, the invention provides a gas sensor including a gas sensing element positioned at least partially within a body and being exposed at a first end to measure a gas in contact with the first end. The gas sensing element defines an axial direction. A flange extends from the body in a direction transverse to the axial direction. The flange has a first side facing toward the first end and a second side facing toward a remote end of the gas sensor. An O-ring seal is configured to sealingly position the gas sensor within a bore. A connector housing is overmolded onto the body to enclose the flange on both the first and second sides. The connector housing is molded to include an insertion portion configured to hold the O-ring seal, and a plug connector portion partially enclosing a plurality of electrical terminals electrically connected to the gas sensing element.

BRIEF DESCRIPTION OF THE DRAWINGS

FIG. 6 is a front view of an intake gas sensor, according to one aspect of the invention.

FIG. 7 is a cross-section view of the intake gas sensor of FIG. 6.

FIG. 8 is a front view of an intake gas sensor, according to one aspect of the invention.

FIG. 9 is a cross-section view of the intake gas sensor of FIG. 8.

FIG. 10 is a front view of an intake gas sensor, according to one aspect of the invention.

FIG. 11 is a cross-section view of the intake gas sensor of FIG. 10.

FIG. 12 is a front view of an intake gas sensor, according to one aspect of the invention.

FIG. 13 is a cross-section view of the intake gas sensor of FIG. 12.

FIG. 14 is a front view of an intake gas sensor, according to one aspect of the invention.

FIG. 15 is a cross-section view of the intake gas sensor of FIG. 14.

FIG. 19 is a cross-section view of the intake gas sensor of FIG. 16.

FIG. 20 is a cross-section view of the sensor assembly of the intake gas sensor of FIG. 16.

FIG. 22 is a perspective view of a housing portion of the intake gas sensor of FIG. 21.

FIG. 23 is a second perspective view of the housing portion of FIG. 22.

FIG. 24 is a cross-section view of the housing portion of FIGS. 22-23.

DETAILED DESCRIPTION

Figure 1:
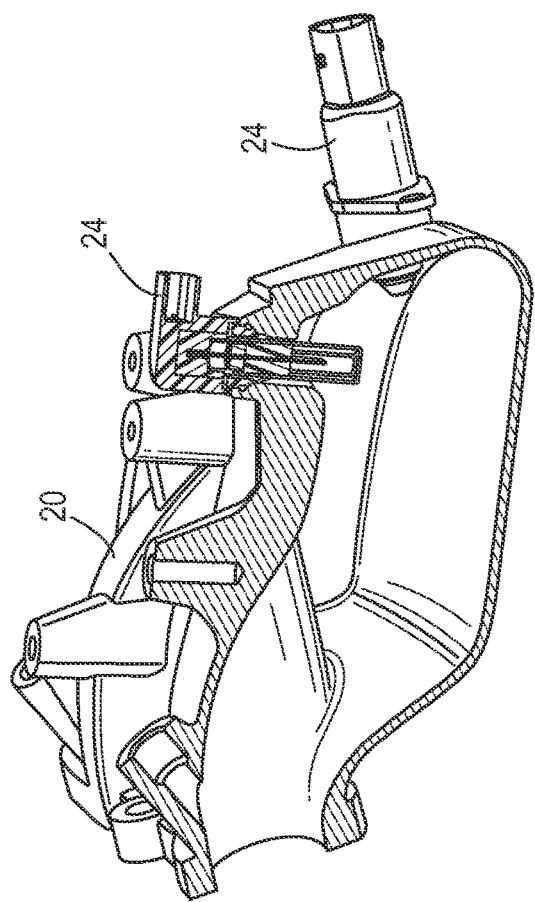
FIG. 1 is a perspective view of an intake manifold for an internal combustion engine, including exemplary mounting locations for a gas sensor.

Before any embodiments of the invention are explained in detail, it is to be understood that the invention is not limited in its application to the details of construction and the arrangement of components set forth in the following description or illustrated in the Mowing drawings. The invention is capable of other embodiments and of being practiced or of being carried out in various ways.

If an oxygen sensor is used in a non-exhaust gas system application such as in an intake manifold, the temperature requirements are lower than in the exhaust stream. Typically the maximum temperature is 130 C. The lower temperature requirement allows the use of less costly and non-traditional materials for oxygen sensors. These materials can include plastics such as thermoplastics. The use of thermoplastics can reduce weight and reduce costs.

The invention provides for making a smaller, lighter weight sensor incorporating a plastic connector housing and overcoming the thermal problems. The mounting method of the sensor can be more flexible than standard oxygen sensors. The integral plug housing eliminates the need for a wire harness in the sensor. Exemplary gas sensors are illustrated in the drawings. Each of the constructions features a plastic housing of one or more pieces, which can be composed of for example, a glass-filled thermoplastic material such as PPS-GF or PBT-GF (e.g., about 25 percent to about 50 percent glass fill).

Figure 3:
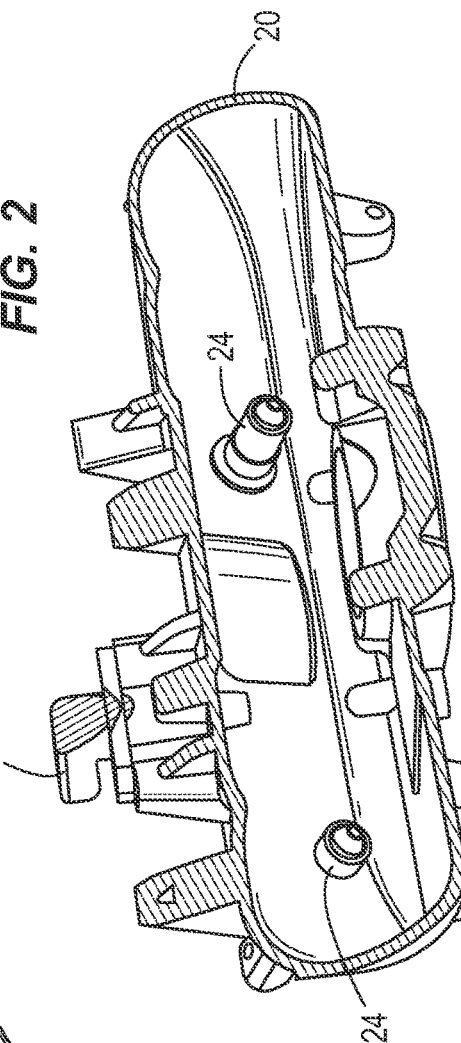
FIG. 3 is a second cross-section view of the intake manifold of FIG. 1.
Figure 2:
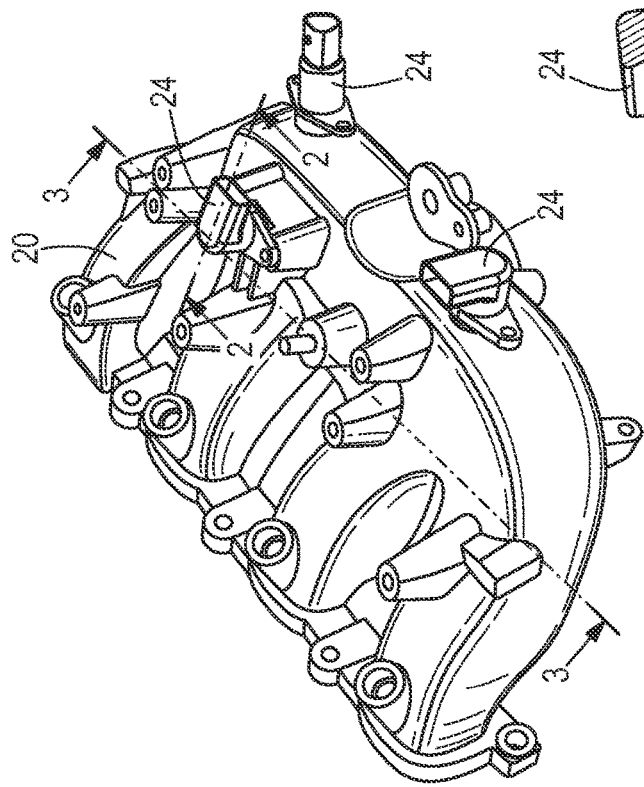
FIG. 2 is a first cross-section view of the intake manifold of FIG. 1.

FIGS. 1-3 illustrate an air intake manifold 20 for an internal combustion engine. A plurality of gas sensors 24 are coupled to the intake manifold 20 to illustrate a variety of exemplary mounting positions, but it should be understood that any number of gas sensors can be provided in the intake manifold 20 (e.g., a single one), and the position of the gas sensor 24 is not necessarily limited to the locations shown in FIGS. 1-3. FIGS. 4-15 illustrate specific gas sensors of various constructions in more explicit detail, each of which can be used in an intake manifold such as the manifold 20 of FIGS. 1-3, another location along the intake path of an internal combustion engine, or another low temperature (non-exhaust) environment.

Figure 5:
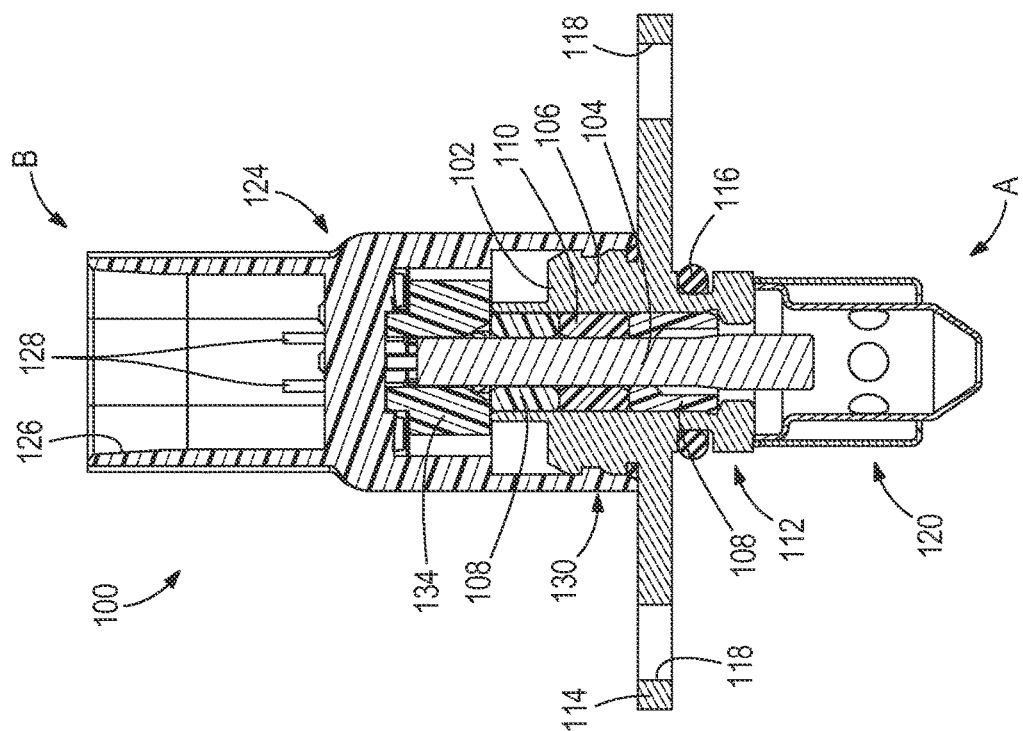
FIG. 5 is a cross-section view of the intake gas sensor of FIG. 4.
Figure 4:
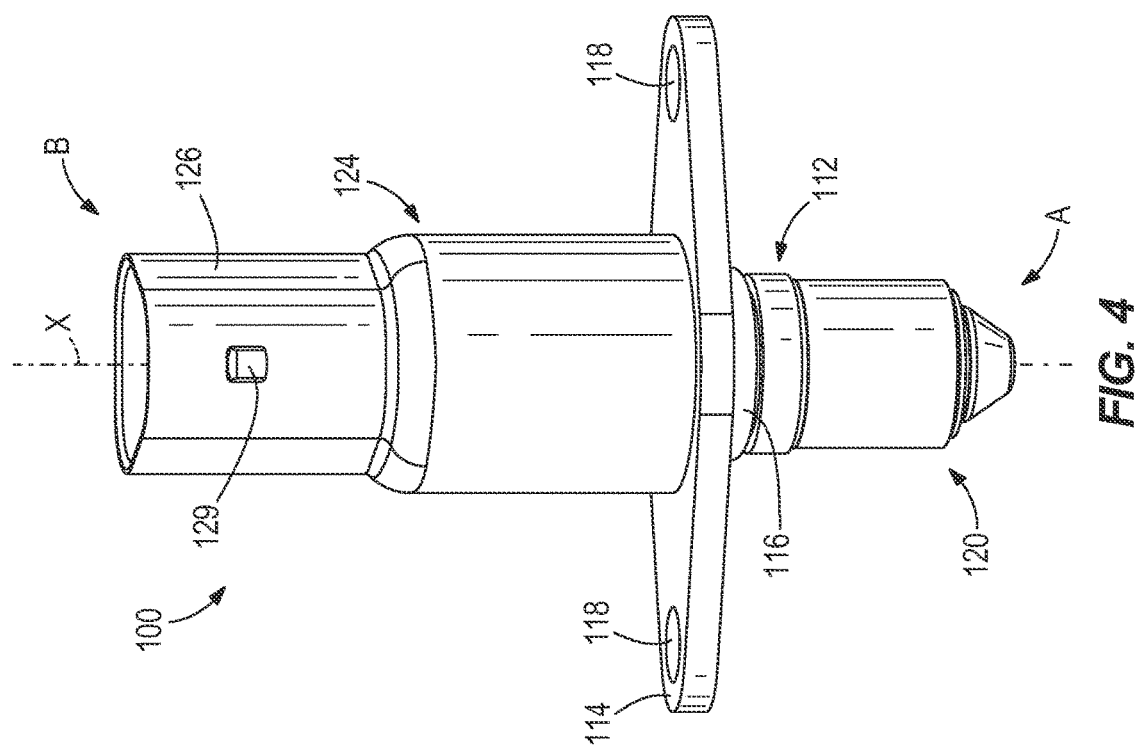
FIG. 4 is a front view of an intake gas sensor, according to one aspect of the invention.
Figure 16:
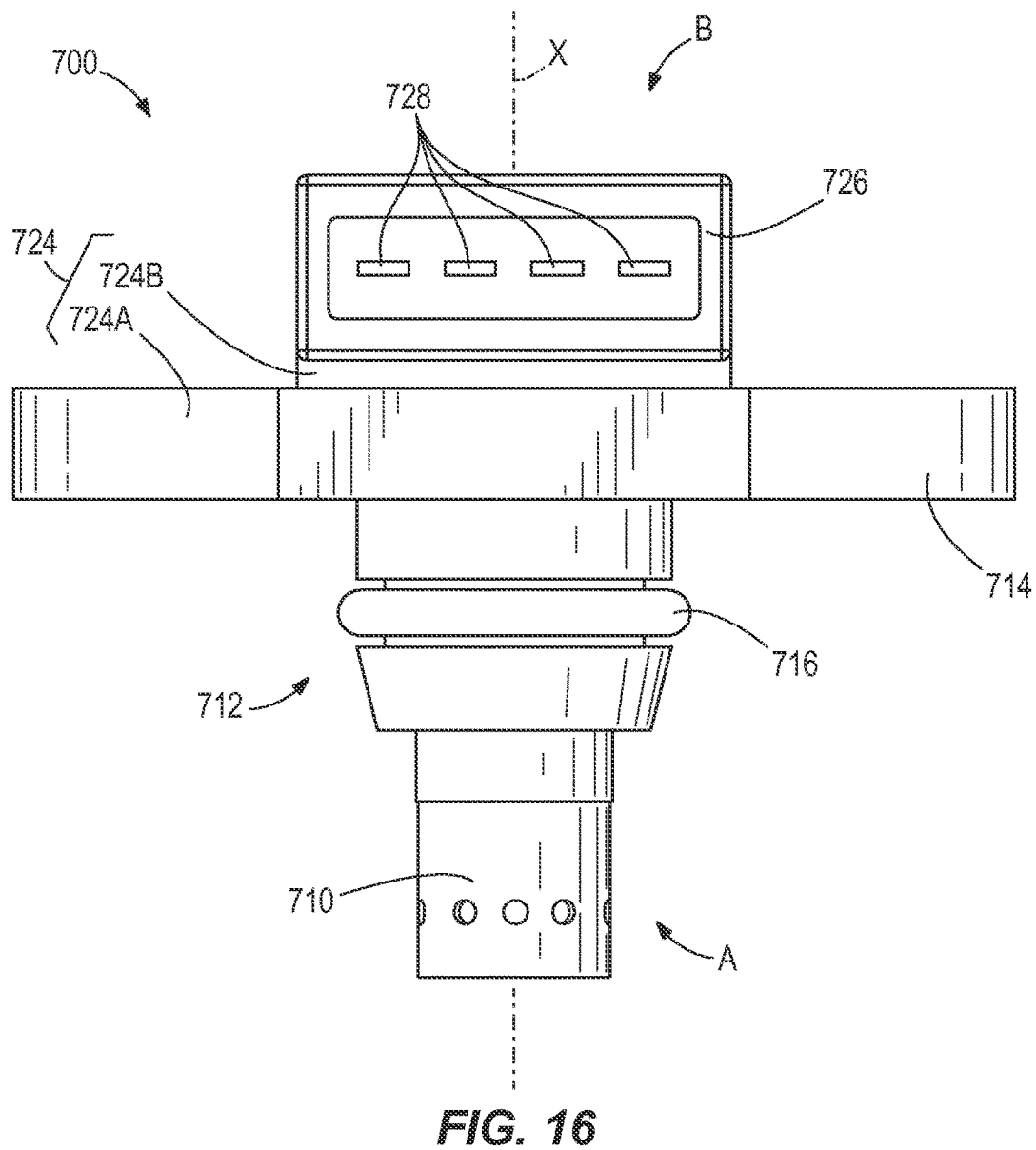
FIG. 16 is a front view of an intake gas sensor, according to one aspect of the present invention.
Figure 17:
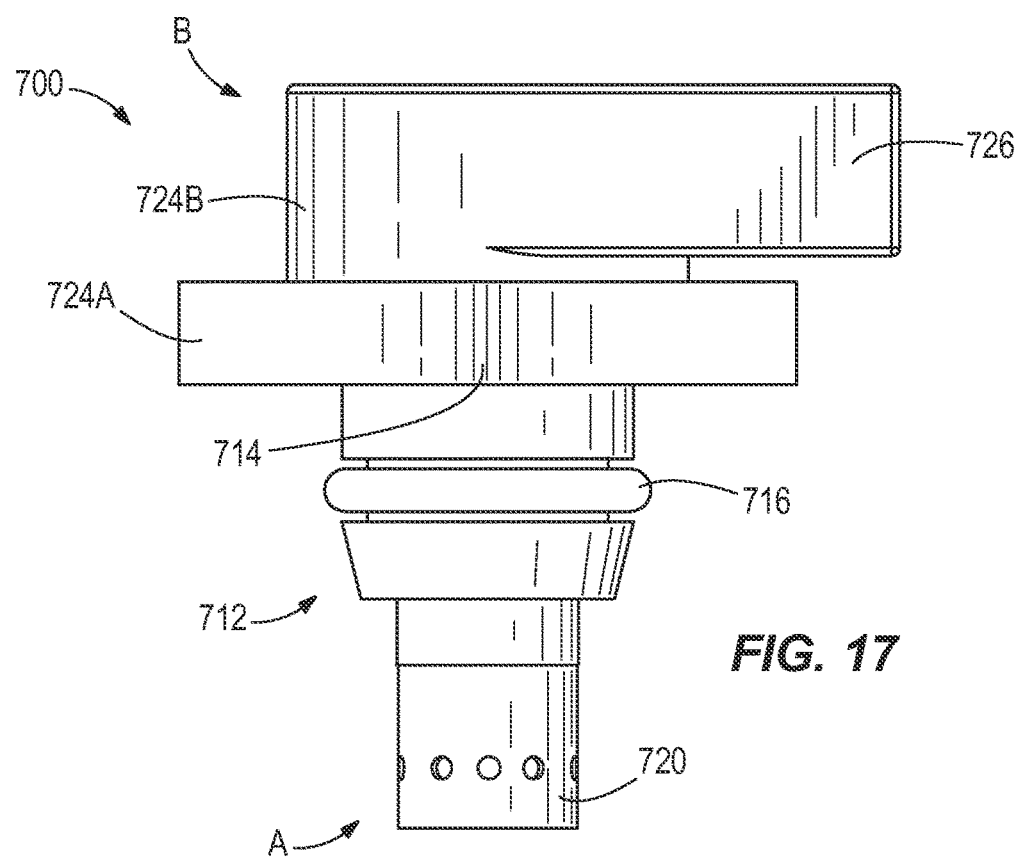
FIG. 17 is a side view of the intake gas sensor of FIG. 16.
Figure 18:
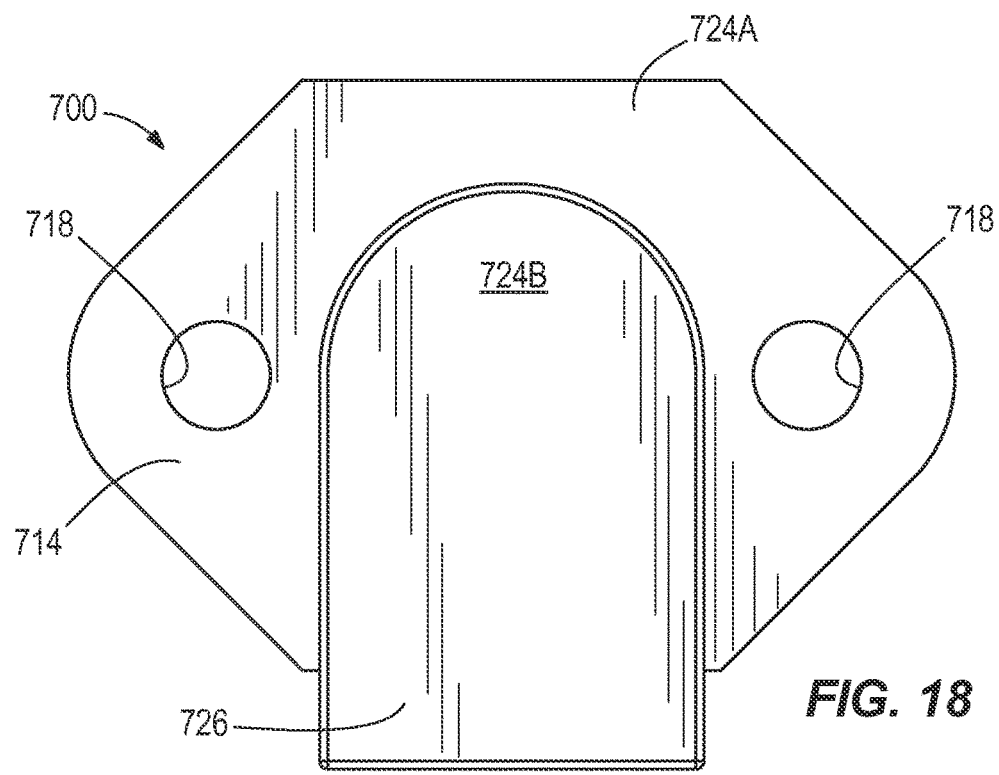
FIG. 18 is a top view of the intake gas sensor of FIG. 16.
Figure 21:
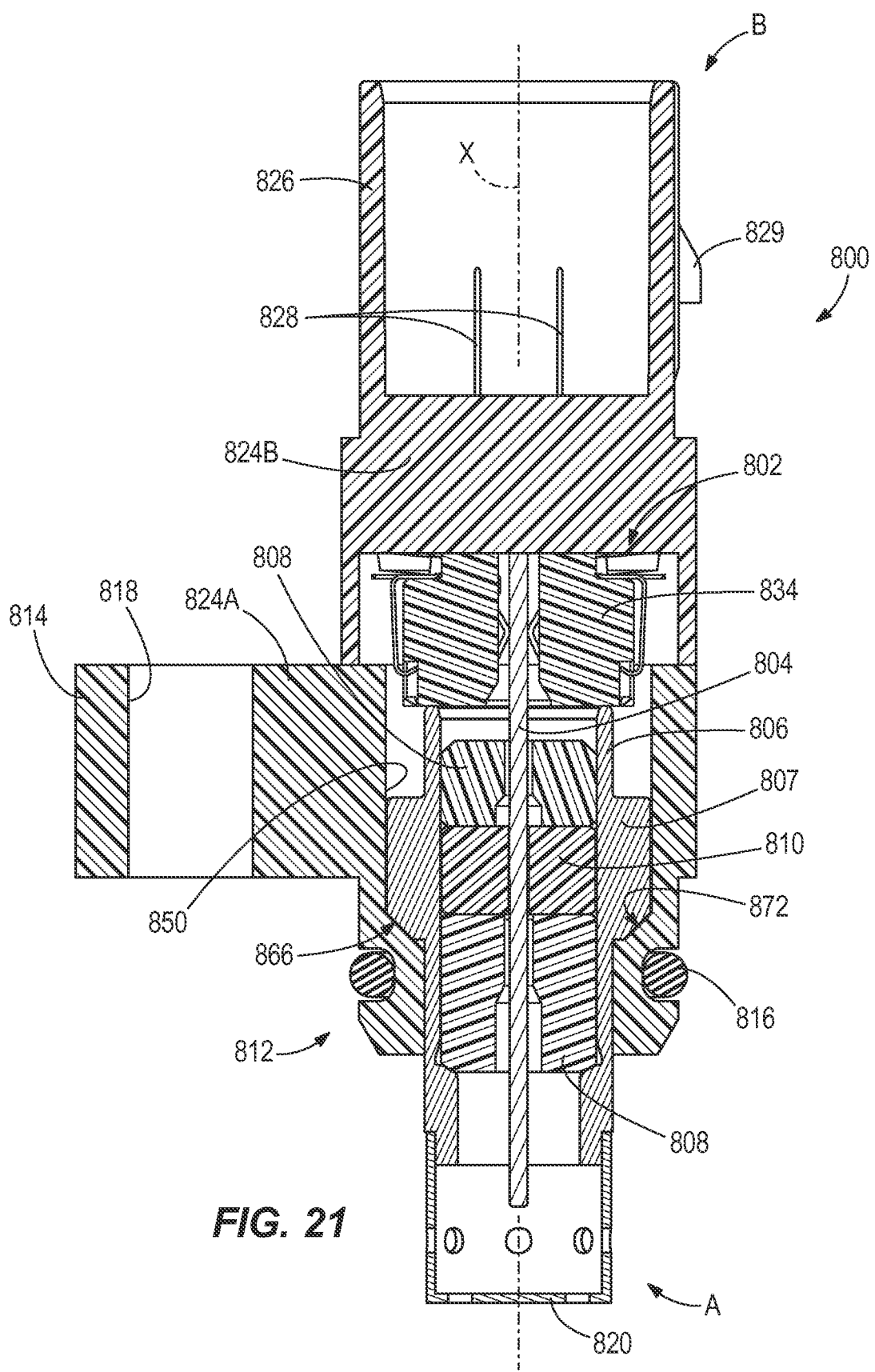
FIG. 21 is a cross-section view of an intake gas sensor, according to a second aspect of the invention.

FIGS. 4 and 5 illustrate a gas sensor 100 according to a first construction. The gas sensor 100 is particularly adapted for use in a low temperature (non-exhaust) environment. The gas sensor 100 includes a sensor subassembly (or "short sensor assembly") 102 that includes a gas sensing element 104 positioned within a sensor sub-housing or body 106 and defining an axis X. The body 106 can be metallic. Ceramic bushings 108 and a soft ceramic seal packing 110 can be used to position the gas sensing element 104 within the body 106. The body 106 includes an insertion portion 112 and a transverse flange 114. The insertion portion 112 receives an O-ring 116, and is configured to be received within a bore in the intake manifold 20 in sealing relationship. The insertion portion 112 and the O-ring 116 allow the sensor 100 to simply "plug into" a bore in the intake manifold 20 (e.g., simple axial insertion into anon-threaded bore). The flange 114 can include one or more apertures 118 to receive fasteners (not shown) for securing the sensor 100 to the intake manifold 20 or other structure. A gasket may also be provided between the flange 114 and the intake manifold 20. One or more protection tubes 120 at a first end or sensing end A of the gas sensor 100 cover a sensing end of the sensing element 104, while allowing fluid communication with passing gases. The first end of the sensing element 104 extends from the body 106 and, except for the protection tube(s) 120, is otherwise exposed to ambient gas. When energized, the sensor subassembly 102 enables a gas sensing function of the gas sensor 100 (e.g., an oxygen sensor, such as a pumped-reference wide-band oxygen sensor).

At a second end B of the gas sensor 100 opposite the sensing end A, a connector housing 124 is coupled to the body 106 to cover the remote or interior end of the sensing element 104 and provide a plug housing or plug connector portion 126 and electrical terminals or connectors 128 for connection with an external plug member at the remote end B of the gas sensor 100. The connector housing 124 can be molded from plastic (examples above), and the electrical connectors 128 can be insert molded therein, leaving the ends exposed for making electrical contact. At least one releasable locking feature 129 (e.g., tab, recess, barb, spring clip, etc.) may be provided on the plug connector portion 126 for releasably locking an external plug member or wire harness in a position that establishes and maintains electrical contact between the electrical connectors 128 and corresponding connectors of the external plug member. In the illustrated construction, the connector housing 124 is provided with one or more internal features providing a snap-fit locking interface 130 with one or more external features of the body 106. Thus, no fasteners are required. In some constructions, no bonding agents or further bonding processes are required. A contact holder or retainer element 134 is provided at the remote or interior end of the sensing element 104. The retainer element 134 can lockingly engage interior ends of the electrical connectors 128 to ensure that proper contact for electrical conduction is maintained between the electrical connectors 128 and conductive pads or portions of the sensing element 104. The electrical connectors 128 can be provided with locking tabs for this purpose.

FIGS. 6 and 7 illustrate a gas sensor 200 according to a second construction. The gas sensor 200 is particularly adapted for use in a low temperature (non-exhaust) environment. Features of the gas sensor 200 that are similar to the gas sensor 100 are not described in detail again, and similar reference numbers are used, incremented by 100.

The connector housing 224, in addition to providing the plug connector portion 226 for connection to an external plug member, also includes an integral (e.g., integrally molded as a single piece) contact holder or retainer portion 234 on an interior thereof. The contact holder portion 234 of the connector housing 224 receives the remote or interior end of the sensing element 204 and maintains contact between the interior ends of the electrical connectors 228 and the conductive portions of the sensing element 204 to ensure electrical connection is maintained.

FIGS. 8 and 9 illustrate a gas sensor 300 according to a third construction. The gas sensor 300 is particularly adapted for use in a low temperature (non-exhaust) environment. Features of the gas sensor 300 that are similar to the gas sensor 100 are not described in detail again, and similar reference numbers are used, incremented by 200.

The connector housing 324 is provided separately from a sleeve 325 that engages the body 306 of the sensor subassembly 302. The sleeve 325, which can be constructed of metal or plastic, provides the interface 330 with the body 306. The interface 330 can be a snap-fit locking interface as shown and described above. Alternately, the sleeve 325 can be secured to the body 306 without a mechanical snap-fit (e.g., bonded or welded). The sleeve 325 is provided with an opening that allows the sleeve 325 to slip over the connector housing 324 and retain a flange or shoulder 327 of the connector housing 324. Although not illustrated, a plug housing portion can also be provided to partially enclose the electrical connectors 328 held by the contact holder portion of the connector housing 324, and to provide a means for coupling an external plug member. The plug housing portion can be formed separately from the illustrated connector housing 324, and assembled therewith, or can be overmolded to become integral therewith. Like the plug housings illustrated in the previous figures, the plug housing portion provides a socket partially enclosing the exposed electrical connectors 328. The plug housing may or may not enclose all or a portion of the sleeve 325 in addition to the connector housing 324.

FIGS. 10 and 11 illustrate a gas sensor 400 according to a fourth construction. The gas sensor 400 is particularly adapted for use in a low temperature (non-exhaust) environment. Features of the gas sensor 400 that are similar to the gas sensors described above are not described in detail again, and similar reference numbers are used, taken from the 400's.

The body 406 of the sensor subassembly 402 may be provided separately from the transverse flange 414, which may be of metallic or plastic construction. The body 406 includes a small flange 407 for abutting the flange 414 on one side and abutting a thin-walled sleeve 425 on the opposite side. The sleeve 425 may be welded or otherwise secured to the body 406. Adjacent the remote end B, opposite the sensing end A of the sensor 400, the sleeve 425 includes an engagement feature 427 particularly adapted for interlocking with the connector housing 424 when overmolded thereon. In the illustrated construction, the engagement feature 427 includes a wall profile having a convoluted shape (e.g., a substantially 180 degree U-shaped bend when viewed in cross-section). However, the engagement feature 427 may take other forms, suitable for receiving an overmolded connector housing 424 to lock together therewith. As illustrated, the connector housing 424 only covers an upper end of the sleeve 425, leaving the outer surface of the sleeve 425 to define an exposed outer surface of the gas sensor 400 between the connector housing 424 and the flange 414. These features described above may provide a narrower overall dimension of the sensor 400.

FIGS. 12 and 13 illustrate a gas sensor 500 according to a fifth construction. The gas sensor 500 is particularly adapted for use in a low temperature (non-exhaust) environment. Features of the gas sensor 500 that are similar to the gas sensors described above are not described in detail again, and similar reference numbers are used, taken from the 500's.

The connector housing 524 of the sensor 500 is provided with an angled plug connector portion 526, which orients the socket and exposed electrical connectors 528 at a non-parallel (i.e., non-zero) angle with respect to the axis X defined by the sensing element 504 and the body 506. In the illustrated construction, the socket and exposed electrical connectors 528 are oriented at a 90-degree angle with respect to the axis X. Other angular orientations (e.g., 30 degrees, 45 degrees, 60 degrees, etc.) are optional, and may be determined by packaging constraints or conveniences of a particular application. The transverse flange 514 for axially securing the sensor 500 with respect to the intake manifold 20 can be provided as an integral portion (e.g., molded as a single piece) with the connector housing 524. The insertion portion 512, which carries the O-ring 516 can also be provided as an integral portion (e.g., molded as a single piece) with the connector housing 524. The body 506 of the sensor subassembly 502 includes a transverse flange 507 that is overmolded with the plastic of the connector housing 524 to lock the sensor subassembly 502 in position with respect to the connector housing 524. For example, first and second sides (e.g., facing the first and second ends A, B of the gas sensor 500) of the transverse flange 507 may be encased or enclosed by the connector housing 524. The body 506 also includes a necked portion adjacent the first side of the transverse flange 507, and the necked portion is substantially enclosed by the connector housing 524.

A contact preform or lead frame 534 may be provided to partially encase each of the electrical connectors 528. The lead frame 534 can be molded onto the interior end of the body 506 or pre-molded and assembled thereon. The lead frame 534 may be a plastic body having the electrical connectors 528 insert molded therein. The connector housing 524 is overmolded onto the lead frame 534 and the body 506 after the lead frame 534 is secured to or positioned on the sensor subassembly 502. The lead frame 534 can be positioned on the body 506 to receive the remote end of the sensing element 504, and may contact the transverse flange 507 when fully seated on the body 506. The connector housing 524 can entirely enclose the lead frame 534.

FIGS. 14 and 15 illustrate a gas sensor 600 according to a sixth construction. The gas sensor 600 is particularly adapted for use in a low temperature (non-exhaust) environment. Features of the gas sensor 600 that are similar to the gas sensors described above are not described in detail again, and similar reference numbers are used, taken from the 600's. The sensor 600 of FIGS. 14 and 15 is similar in many respects to the sensor 500 of FIGS. 12 and 13, except as noted below.

The connector housing 624 is integrally-molded to include the plug connector portion 626, the transverse flange 614, and the insertion portion 612, but rather than being overmolded onto a body of the sensor subassembly 602, the connector housing 624 is overmolded onto an upper end of the protection tube 620 (e.g., an outer protection tube). The protection tube 620 is provided with an engagement feature 627 (e.g., a transverse flange) at its upper or remote end for securely interlocking with the molded connector housing 624. In the illustrated construction, the engagement feature 627 has first and second axially-facing surfaces, similar to the transverse flange 507 of the gas sensor 500, which are both enclosed or encased by the connector housing 624. Thus, the outer protection tube 620 serves as a housing of the sensor subassembly 602, and a body manufactured with a turning operation is not required. The outer protection tube 620 can be formed by deep drawing, as can an inner protection tube 620. The inner protection tube 620 can be pressed with, welded to, or simply held captive by the outer protection tube 620. A single heat-formed glass seal 609 secures and seals the sensing element 604 within the outer protection tube 620, eliminating the need for a compression sealing processing step. The sensor 600 provides substantial material savings, especially compared to a gas sensor suitable for exhaust use.

FIGS. 16-20 illustrate a gas sensor 700 according to a seventh construction. The gas sensor 700 is particularly adapted for use in a low temperature (non-exhaust) environment. Features of the gas sensor 700 that are similar to the gas sensors described above are not described in detail again, and similar reference numbers are used, taken from the 700's. The sensor 700 of FIGS. 16-20 is similar in many respects to the sensor 500 of FIGS. 12 and 13, except as noted below.

The gas sensor 700 includes a two-piece sensor housing 724 that includes a first portion 724A and a second portion 724B that are formed separately and coupled together. The first portion 724A includes an insertion portion 712, which carries the O-ring 716, and further includes the transverse mounting flange 714. The first housing portion 724A includes a bore 750 open toward the remote end B of the sensor 700, opposite the sensing end A. The bore 750 has a transverse surface 752, against which the transverse flange 707 of the body 706 is positioned. The second portion 724B includes a body portion configured to fit into the bore 750 and to abut the transverse flange 707. The transverse flange 707 of the body 706 is trapped between the first and second housing portions 724A, 724B rather than being overmolded by a single housing portion. The second portion 724B of the housing 724 further includes the plug housing 726 for presenting the electrical connectors 728 to an external plug or wire harness. The second portion 724B of the housing 724 can be provided in a variety of different ways, including but not limited to: being overmolded onto the body 706 and the housing first portion 724A, being adhesively bonded to the housing first portion 724A to enclose the body 706, and being welded to the housing first portion 724A to enclose the sensor sub-housing 706. When the first and second housing portions 724A, 724B are coupled, the sensor subassembly 702 is held captive, and need not be bonded or fixed to either housing portion 724A, 724B, although it may be if desired. The electrical connectors 728 can be provided for final assembly with the second housing portion 724B either with or without a separate lead frame.

FIGS. 21-24 illustrate a gas sensor 800 according to an eighth construction. The gas sensor 800 is particularly adapted for use in a low temperature (non-exhaust) environment. Features of the gas sensor 800 that are similar to the gas sensors described above are not described in detail again, and similar reference numbers are used, taken from the 800's. The sensor 800 of FIGS. 21-24 is similar in many respects to the sensors 100 and 700 of FIGS. 4-5 and 16-20, respectively.

Rather than the second housing portion 824B fitting within the bore 850 of the first housing portion 824A, the two housing portions 824A, 824B are mated with a butt-joint in the illustrated construction. The abutting portions can be bonded by adhesive, welding, etc. However, alternate styles of joints between the housing portions 824A, 824B are also contemplated, including any number of known joint styles with overlapping and/or interlocking portions. The second housing portion 824B provides a straight plug housing 826 like that of FIGS. 4-5, which extends generally coaxially or parallel with the axis X, and positions the electrical connectors 828 in a similar orientation. The first housing 824A can have a single-sided flange 814 with a single aperture 818, although other configurations are optional. The bore 850 in the first housing portion 824A is provided with a tapered surface 872 against which a tapered abutment surface 866 of the sensor body 806 rests. The tapered abutment surface 866 is part of a positioning flange or protrusion 807 of the body 806.

It will be appreciated that particular features of any of the above described constructions may be interchanged, where not inherently precluded, to arrive at additional constructions not explicitly shown or described. All these variations are contemplated by the inventors at the time of the invention. This includes, but is not limited to, the orientation or shape of the connector housings, which may take any of the illustrated forms or alternate forms desirable for particular applications, and the manner of coupling and/or retaining a sensor subassembly within one or more molded plastic housings.

Furthermore, any of the gas sensors disclosed herein may include additional features to promote use in a low-temperature environment, such as an intake system of an internal combustion engine. For example, whereas stranded wires pass through a conventional metal-body oxygen sensor to allow pressure equalization between the inside and outside of the sensor housing and to re-supply reference gas to the sensing element, molding a plastic housing over solid electrical terminals provides a hermetic seal which can inhibit such actions. Therefore, a port may be provided in the molded connector housing to establish fluid communication between the cavity surrounding the remote end of the sensing element and the external environment. A membrane may limit the fluid communication through the port. For example, the membrane (e.g., a porous Teflon® membrane) may allow passage of gases (e.g., oxygen, air, etc) while restricting or preventing passage of liquids, such as water or other contaminants. Also, to manage the internal temperature of the gas sensor and prevent overheating of the plastic housing(s), the protection tube(s) may be configured to dissipate heat from an internal sensor heater. This can include providing a heat conduction path from the sensing element and/or heater to the protection tube(s), and can further include providing heat dissipating structures (e.g., fins) on the protection tube(s).

What is claimed is:

1. A gas sensor comprising:
    a gas sensing element positioned at least partially within a body and being exposed at a first end to measure a gas in contact with the first end;
    a sleeve fixed to the body and extending from the body in a direction opposite the first end of the gas sensing element, the sleeve including a remote end portion having an engagement feature; and
    a connector housing overmolded onto the end portion of the sleeve to lock onto the sleeve via the engagement feature, the connector housing including a plug connector portion partially enclosing a plurality of electrical terminals electrically connected to the gas sensing element.

2. The gas sensor of claim 1, further comprising an O-ring seal held by the body and configured to sealingly position the gas sensor within a bore.

3. The gas sensor of claim 2, further comprising a transverse mounting flange extending outward from the body at a position between the plug connector portion and the O-ring seal.

4. The gas sensor of claim 3, wherein the transverse mounting flange is integrally formed as a single piece with the body.

5. The gas sensor of claim 1, wherein the engagement feature includes a wall profile having a convoluted shape.

6. The gas sensor of claim 5, wherein a cross-section of the convoluted shape includes a U-shaped bend.

7. The gas sensor of claim 1, wherein the sleeve is laser welded to the body.

8. The gas sensor of claim 1, wherein the plug connector portion is a straight plug connector, extending in a direction substantially parallel with the gas sensing element.

9. The gas sensor of claim 1, wherein the plug connector portion is an angled plug connector, extending in a direction substantially non-parallel with the gas sensing element.

10. The gas sensor of claim 9, wherein the plug connector portion is a right angle plug connector, extending substantially perpendicular to the gas sensing element.

11. The gas sensor of claim 1, wherein the connector housing is molded from a glass-filled thermoplastic material with glass fill of about 25 percent to about 50 percent.

12. A gas sensor comprising:
    a gas sensing element positioned at least partially within a body and being exposed at a first end to measure a gas in contact with the first end, the gas sensing element defining an axial direction;
    a flange extending outward from the body in a direction transverse to the axial direction, the flange having a first side facing toward the first end and a second side facing toward a remote end of the gas sensor;
    an O-ring seal configured to sealingly position the gas sensor within a bore; and
    a connector housing overmolded onto the body to enclose the flange on both the first and second sides, wherein the connector housing is molded to include
        an insertion portion configured to hold the O-ring seal, and
        a plug connector portion partially enclosing a plurality of electrical terminals electrically connected to the gas sensing element.

13. The gas sensor of claim 12, wherein the body includes a necked portion adjacent the first side of the flange, the necked portion being substantially enclosed by the connector housing.

14. The gas sensor of claim 13, wherein the necked portion is substantially enclosed by the insertion portion of the connector housing.

15. The gas sensor of claim 12, further comprising a lead frame holding the plurality of electrical terminals in a predetermined positional relationship, the lead frame being positionable on the body to receive a remote end of the gas sensing element.

16. The gas sensor of claim 15, wherein the lead frame contacts the second side of the flange when fully seated on the body.

17. The gas sensor of claim 15, wherein the lead frame is entirely enclosed within the connector housing.

18. The gas sensor of claim 12, wherein the connector housing is further molded to include a mounting flange extending transversely from the body.

19. The gas sensor of claim 18, wherein the mounting flange includes at least one mounting aperture configured to receive a fastener.

20. The gas sensor of claim 12, wherein the connector housing is molded from a glass-filled thermoplastic material with glass fill of about 25 percent to about 50 percent.

\* \* \* \* \*